United States Patent [19]

Kunig

[11] Patent Number: 5,046,502
[45] Date of Patent: Sep. 10, 1991

[54] METHOD AND APPARATUS FOR MEASURING CARDIAC EFFICIENCY

[76] Inventor: Horst E. Kunig, R.D. #1, Box 577, Saltsburg, Pa. 15681

[21] Appl. No.: 521,154

[22] Filed: May 9, 1990

Related U.S. Application Data

[63] Continuation-in-part of Ser. No. 468,137, Jan. 22, 1990.

[51] Int. Cl.[5] ................................................ A61B 5/02
[52] U.S. Cl. .................................... 128/670; 128/713; 128/668
[58] Field of Search ................. 128/670, 713, 419 PG, 128/668

[56] References Cited

U.S. PATENT DOCUMENTS

| | | | |
|---|---|---|---|
| 4,197,836 | 4/1980 | Wagner et al. | 128/713 |
| 4,437,469 | 3/1984 | Djordjevich et al. | 128/713 |
| 4,770,177 | 9/1988 | Schroeppel | 128/670 |
| 4,858,618 | 8/1989 | Konno et al. | 128/713 |
| 4,899,751 | 2/1990 | Cohen | 128/419 PG |

Primary Examiner—Francis Jaworski
Assistant Examiner—George Manuel
Attorney, Agent, or Firm—Clifford A. Poff

[57] ABSTRACT

A monitoring device for cardiac efficiency receives signals representative of volume and pressure of the ventricle, oxygen consumption and heart rate and processes these signals to determine distinct energy levels during a cardiac cycle to delineate preload and afterload potentials. Cardiac efficiency is then determined as the energy transferred in a transition from the preload level to the afterload level as related to the preload level. Circulatory efficiency is determined as the ratio of transition energy over metabolic rate. Stroke and cardiac deficiency are determined by the ratio of stroke and cardiac preload/afterload potential band overlap divided by maximum stroke and cardiac preload potential, respectively. Circulatory deficiency is determined by the ratio of cardiac preload/afterload potential band overlpa divided by the metabolic rate.

21 Claims, 8 Drawing Sheets

× EDVI × SBP
⊗ EDVI × DBP
• ESVI × SBP
⊙ ESVI × DBP

FIG. 3A

× STROKE TRANSITION
  ENERGY
• STROKE WORK

METHOD AND APPARATUS FOR MEASURING CARDIAC EFFICIENCY

CROSS REFERENCE TO RELATED APPLICATION

This Application is a Continuation-in-part of application Ser. No. 468,137, filed Jan. 22, 1990.

1. Field of the Invention: The present Invention relates in general to a cardiac monitor and, more particularly to a method and apparatus for determining the efficiency of the heart based on blood volume and the pressure created by the pumping function of the heart.

2. Description of the Prior Art: Generally, the performance of the heart is described by a variety of hemodynamic parameters. They include stroke volume, heart rate and blood pressure, which are primary measurements from which other parameters such as cardiac work and resistance are derived. While such measurements reflect the performance of the heart at the time of the measurement they do not provide an indication of the efficiency of the heart as a pump.

Attempts to assess cardiac status have included cardiac work determined as the product of cardiac output and mean blood pressure, systemic vascular resistance, pulmonary vascular resistance, and the establishment of ventricular function curves.

Further attempts to assess the efficiency of the heart included measurement of the ejection fraction. When the heart proceeds from the end-diastolic state to the end-systolic state, blood is expelled into the circulatory system. The volume of blood expelled related to the volume of the ventricle before expulsion defined as the volume ejection fraction is considered currently as a measure of cardiac efficiency.

The volume ejection fraction relates strictly to the changes in volume. As a pump, the heart also develops pressure which must be taken into account when determining cardiac efficiency. The ejection fraction considering only the volume of expelled blood in relation to the ventricle volume before expulsion is therefor, an inadequate measure of heart efficiency.

In addition to the volume ejection fraction, a pressure ejection fraction may be defined as the ratio of the difference of the systolic blood pressure minus the diastolic blood pressure divided the systolic blood pressure. The pressure ejection fraction is as limited as the volume ejection fraction to describe the true efficiency of the heart. However, the volume ejection fraction and the pressure ejection fraction have utility as a trend indicator. The product of volume and pressure equates with energy and specifically the capability of doing work.

It is an object of the present invention to provide an apparatus to facilitate a true and accurate efficiency evaluation of the heart performance by a simultaneous analysis of volume and operating pressure condition in form of energy of ejection in relation to the energy contained in the heart prior to ejection whereby the status of cardiac health of a subject and the time trend of cardiac health may be objectively assessed by heart efficiency measurements.

It is also an object of the invention to provide an apparatus for monitoring the efficacy of medical interventions by heart efficiency measurements.

Another object of the invention is to provide an apparatus to determine and monitor the circulatory efficiency as the ratio of the energy expelled by the heart to the total energy consumed by the body as measured by the total body oxygen consumption.

It is still another object of the invention to provide an apparatus for determining the onset of inefficiency of the heart when pre-ejection energies and post-ejection energies overlap.

SUMMARY OF THE PRESENT INVENTION

In accordance with the present invention an apparatus is disclosed for diagnosing the efficiency of the heart of an individual and changes of that efficiency with respect to medical interventions.

According to the present invention there is provided a cardiac monitoring device for determining efficiency of the heart of an individual, the device including means for generating signals representative of end-diastolic volume, end-systolic volume, systolic blood pressure, and diastolic blood pressure, and means responsive to such signals for producing signals corresponding to stroke preload and stoke afterload potentials.

More specifically, in one cardiac cycle the ventricle fills with blood to reach the end-diastolic volume (EDV) at a low diastolic blood pressure (DBP). Upon isovolumetric contraction the pressure in the ventricle rises to a higher systolic blood pressure (SBP). Following is the expulsion of blood where the ventricle acquires the smaller end-systolic volume (ESV) without changing the systolic blood pressure (SBP). To complete the cardiac cycle the ventricle pressure decreases to a low pressure (DBP) while the ventricle volume remains unchanged. The energy difference (EDV * SBP)−(ESV * DBP) is expelled with the expulsion of blood when the heart transfers from the state of highest energy given by the product (EDV * SBP) to the state of lowest energy given by the product (ESV * DBP). According to the present invention an apparatus is disclosed to determine the four distinct energy states (EDV * SBP), (EDV * DBP), (ESV * SBP), and (ESV * DBP) and the transition energy given by (EDV * SBP)−(ESV * DBP).

In the preferred embodiment further means are provided to determine the efficiency of the heart as the ratio of the transition energy over the highest energy state of (EDV * SBP) which was necessary to produce such an energy transfer.

Also in the preferred embodiment, means are disclosed to convert transition energies and heart efficiencies as they occur in one beat to corresponding values per one minute by multiplication by the heart rate and subsequently derive circulatory efficiencies by correlating these values to total body oxygen consumption or metabolic rate.

BRIEF DESCRIPTION OF THE DRAWINGS

These features and advantages of the present invention as well as others will be more fully understood when the following description is read in light of the accompanying drawings, in which.

DESCRIPTION OF THE PREFERRED EMBODIMENT

Figure 1:
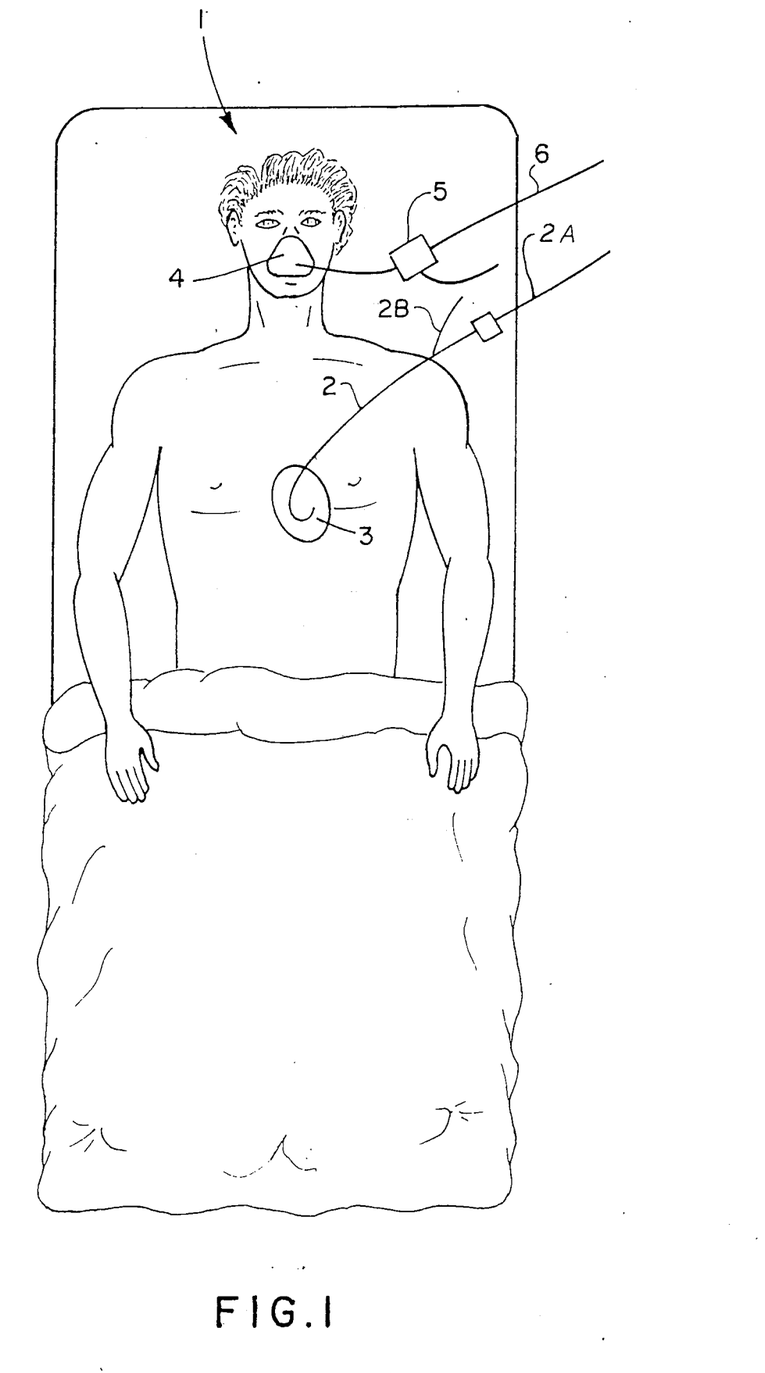
FIG. 1 illustrates a subject in whom a catheter is implanted in the heart for generating volume and pressure data and a mask placed over mouth and nose for sampling inspired and expired gases to determine total body oxygen consumption.

Referring to FIG. 1 there is illustrated a subject 1 with an implanted pulmonary artery ejection fraction catheter 2. The catheter embodies a known construction for use to generate signals in wire cable 2A representative of systolic and diastolic pulmonary artery pressures, SBP and DBP, respectively, and heart rate (HR). Also, upon injection of a cold bolus via catheter duct 2B signals are generated representative of temperature changes as sensed by a thermistor 3 located in the tip portion of the catheter. Such temperature changes are used to generate signals representative of stroke volume (SV), volume ejection fraction EF(V), end-diastolic volume (EDV) and end-systolic volume (ESV). A mask 4 is placed over the mouth and nose of a subject and is connected by a duct to a sensor 5 to generate signals in line 6 representative of the oxygen content of the inspired and expired gases. The oxygen content signals are used to determine the oxygen consumption and metabolic rate.

Figure 2:
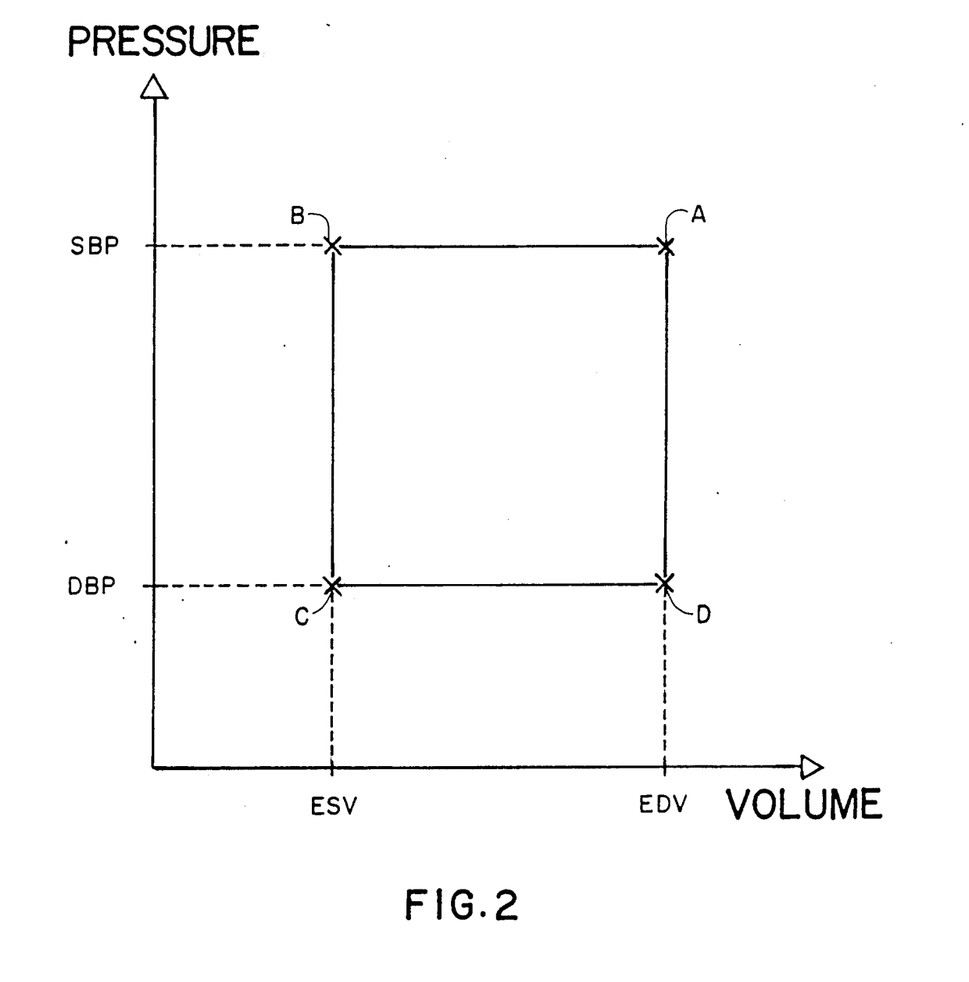
FIG. 2 illustrates the volume $V_2$ pressure relationship during one cardiac cycle.

Referring now to FIG. 2 there is shown in a cartesian coordinate system the relationship between volume and pressure during one cardiac cycle. Four distinct points labelled A, B, C, and D may be recognized. The points of the cardiac cycle have associated four distinct energies; namely point A, is the highest energy level given by the product of the magnitude of the end diastolic volume multiplied by the systolic blood pressure i.e. (EDV * SBP). Point B is a high energy level given by the product of the magnitude of end systolic volume (ESV) multiplied by the systolic blood pressure (SBP) i.e. (ESV * SBP). Point C is the lowest energy level given by the product of the magnitude of end systolic volume (ESV) multiplied by the dioslatic blood pressure (DBP) i.e., (ESV * DBP). Point D is a low energy level given by the product of the magnitude of the end diastolic volume (EDV) multiplied by the diastolic blood Pressure (DBP) i.e. (EDV * DBP).

Four transitions may, thus, be recognized during the completion of one cardiac cycle, namely A to B, B to C, C to D, and D to A. Each transition is associated with a distinct energy change. Since the transition from D to A occurs without change in ventricular volume and at a time prior to expulsion of blood from the ventricle, an energy band may be defined bordered by the two energy levels of the two points D and A, i.e., (EDV * DBP) and (EDV * SBP) which henceforth will be referred to as the stroke preload potential band. Similarly, since the transition from points B to C also occurs without change in volume, however, at a time after expulsion of blood from the ventricle, an energy band may be defined as comprised of the products of (ESV * SBP) and (ESV * DBP), respectively, which establish the borders of a stroke afterload potential band.

In The following table 1, there are listed hemodynamic values for normals (N) taken from a published paper by S. S. Yang, et al. *From Cardiac Catheterization Data to emodynamic Parameters:*, F. A. Davis Co., Philadelphia, PA 1978 and Patients (P) from a published paper by J. W. Biondi, et al. *The effect of Incremental Positive End-Expiratory Pressure on Right Ventricular Hemodynamic and Ejection Fraction* Analg. 1988; 67:144-151.

TABLE 1

|  | Units of measures | N | P |
|---|---|---|---|
| cardiac Index CI | l/min sqm | 3.2 | 3.5 |
| heart Rate HR | b/min | 70 | 103 |
| stroke index SVI = CI/HR = EDVI − ESVI | ml/b sqm | 45 | 34 |
| end diastolic volume index EDVI | ml/b sqm | 64 | 113 |
| end systolic volume index ESVI | ml/b sqm | 19 | 79 |
| volume ejection fraction EF(V) = (EDVI − ESVI)/EDVI | % | 70 | 30 |
| systolic pulmonary artery pressure SBP | mm Hg | 25 | 48 |
| diastolic pulmonary artery pressure DBP | mm Hg | 12 | 12 |
| mean pulmonary pressure MAP | mm Hg | 16 | 24 |
| pressure ejection fraction EF(P) = (SBP − DBP)/SBP | % | 52 | 75 |
| stroke work SVI * MAP | Mergs/b sqm | 0.96 | 1.1 |
| cardiac work SVI * MAP * HR | kcal/h sqm | 0.097 | 0.16 |
| basal metabolic rate $Vo_2$ BMR = $(VO_2)_{min}$ Male 40y age | kcal/h sqm | 38 | 38 |

Figure 3A:
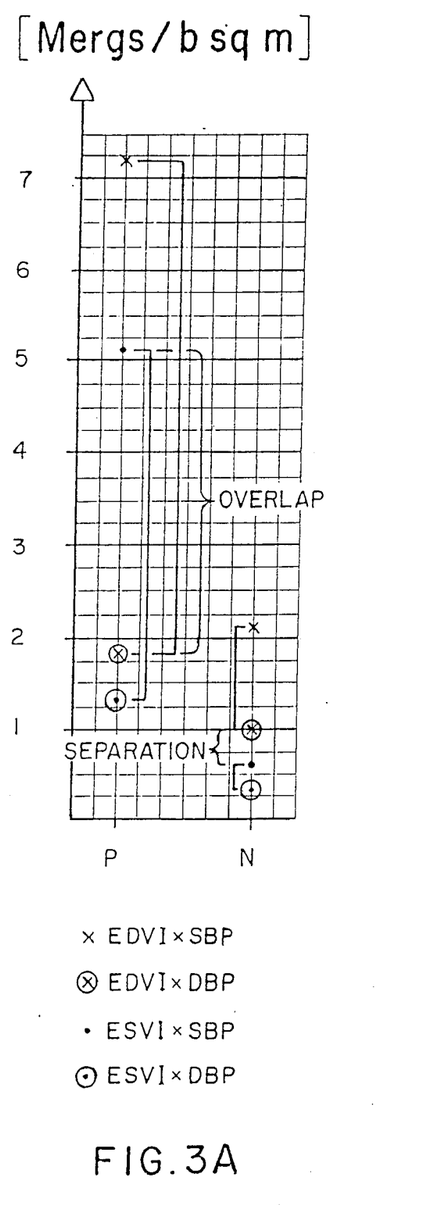
FIG. 3A illustrates plot points for the stroke preload and afterload potentials for normals (N) and patients (P)

Using the data given in table 1 it can be seen from FIG. 3A that the stroke preload band for normals (N) as defined by the potentials (EDVI * SBP)=2.1 Mergs/b sq m and (EDVI * DBP)=1.0 Mergs/b sq m, wherein Mergs is $10^6$ ergs, b is beats and sq m is square meters. The stroke afterload band for normals (N) as defined by the potentials (ESVI * SBP)=0.6 Mergs/b sq m and (ESVI * DBP)=0.3 Mergs/b sq m. The difference OL=(EDVI * DBP)−(ESVI * SBP) indicates the separation of the preload band from the afterload band. If OL>0 then preload-and afterload bands are separated. If OL<0 then preload- and afterload bands overlap. Specifically, preload and afterload band are separated by 0.4 Mergs/b sq m for this normal subject. Based on the data in table 1 the preload and afterload bands for Patient (P) overlap by 3.3 Mergs/b sq m.

Tables 2-4 as derived from the hemodynamic data given in table 1 for a normal subject (N) and in a patient (P) are process according to the instant invention to yield the data listed as stroke values (for each beat) in table 2, cardiac values (for each minute) in table 3, and circulatory valves (in reference to basal metabolic rate) in table 4.

TABLE 2
STROKE VALUES

| | Units of measure | N | P |
|---|---|---|---|
| stroke preload potentials | | | |
| EDVI * SBP | Mergs/b sqm | 2.1 | 7.2 |
| EDVI * DBP | Mergs/b sqm | 1.0 | 1.8 |
| stroke afterload potentials | | | |
| ESVI * SBP | Mergs/b sqm | 0.6 | 5.1 |
| ESVI * DBP | Mergs/b sqm | 0.3 | 1.3 |
| stroke preload/afterload band separation OL = (EDVI * DBP) − (ESVI * DBP) | Merqs/b sqm | +0.4 | −3.3 |
| stroke transition energy STE = (EDVI * SBP) − (ESVI * DBP) − −OL; OL < 0 | Mergs/b sqm | 1.8 | 2.6 |
| stroke efficiency SEF = STE/(EDVI * SBP) | % | 86 | 36 |
| stroke deficiency SDF = −OL/(EDVI * SBP) | % | 0 | 46 |

TABLE 3
CARDIAC VALUES

| | Units of measure | N | P |
|---|---|---|---|
| cardiac preload potentials | | | |
| EDVI * SBP * HR | kcal/h sqm | 0.21 | 1.07 |
| EDVI * DBP * HR | kcal/h sqm | 0.10 | 0.27 |
| cardiac afterload potentials | | | |
| ESVI * SBP * HR | kcal/h sqm | 0.06 | 0.76 |
| ESVI * DBP * HR | kcal/h sqm | 0.03 | 0.19 |
| cardiac preload/afterload band separation OL = (EDVI * DBP * HR) − (ESVI * SBP * HR) | kcal/h sqm | +0.04 | −0.49 |
| cardiac transition energy CTE = (EDVI * SBP * HR) − −(ESVI * DBP * HR) − OL | kcal/h sqm | 0.18 | 0.39 |
| cardiac efficiency CEF = CTE/(EDVI * SBP * HR) | % | 86 | 36 |
| cardiac deficiency CDF = −OL/(EDVI * SBP * HR) | % | 0 | 46 |

TABLE 4
CIRCULATORY VALUES

| | Units of measure | N | P |
|---|---|---|---|
| circulatory preload potentials | | | |
| (EDVI * SBP * HR)/VO$_2$ | % | 0.55 | 2.8 |
| (EDVI * DBP * HR)/VO$_2$ | % | 0.26 | 0.7 |
| circulatory afterload potentials | | | |
| (ESVI * SBP * HR)/VO$_2$ | % | 0.16 | 2.0 |
| (ESVI * DBP * HR)/VO$_2$ | % | 0.08 | 0.5 |
| circulatory efficiency CIEF = CTE/VO$_2$ | % | 0.47 | 1.0 |
| circulatory deficiency CIDF = OL/VO$_2$ | % | 0 | 1.29 |

Figure 3B:
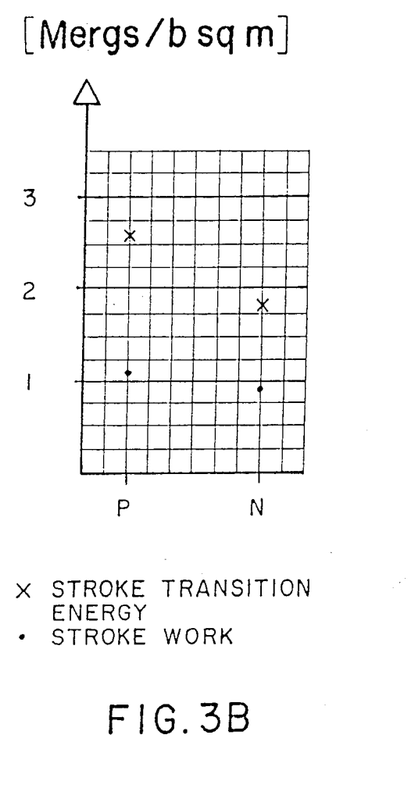
FIG. 3B illustrates plot points for transition energies and stroke work for normals (N) and patients (P)

Referring to FIG. 3B, the stroke transition energy, STE, is defined as the energy released when the heart proceeds from the energy state of the highest preload potential (EDVI * SBP) to the energy state of the lowest afterload potential (ESVI * DBP). However, in cases when the preload potential band and the afterload potential band overlap, no energy is transferred and at this occasion the heart exists simultaneously in the preload and afterload energy state. Hence, the overlap energy, OL, must be subtracted to yield the stroke transition energy as STE=(EDVI * SBP)−(ESVI * DBP)−OL.

Figure 3C:
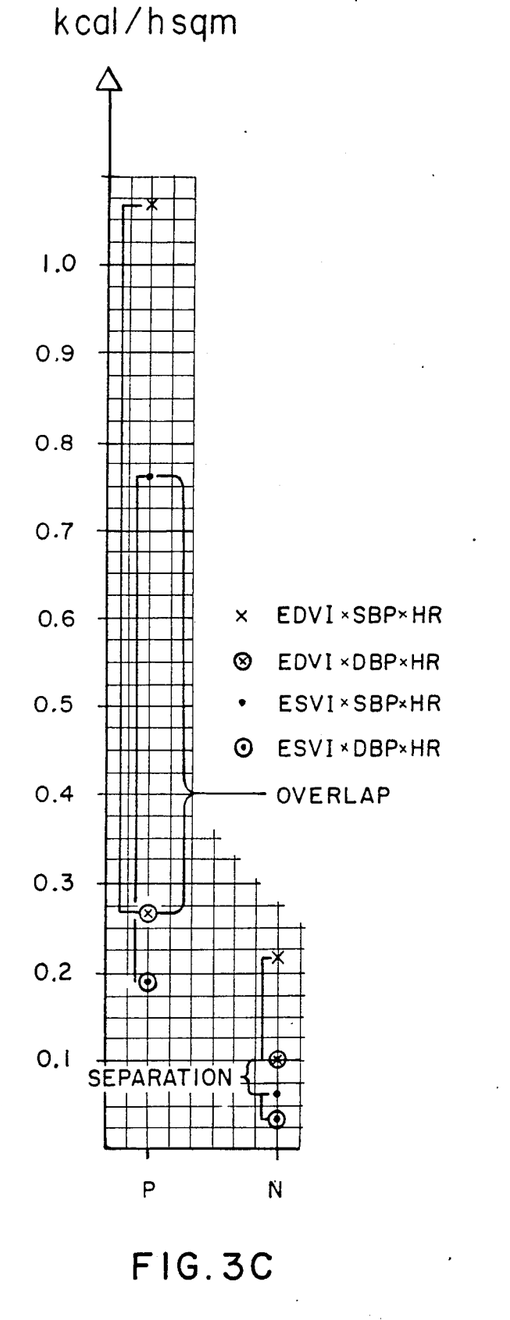
FIG. 3C illustrates plot points for the cardiac preload and afterload potentials for normals (N) and patients (P)
Figure 3D:
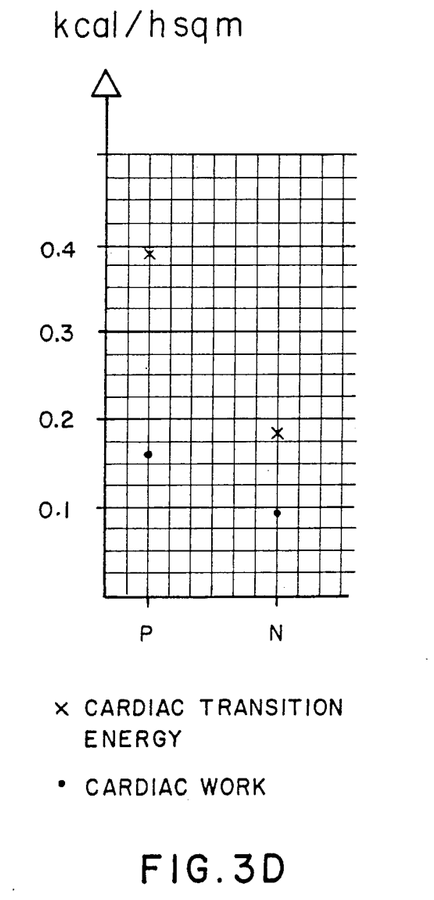
FIG. 3D illustrates plot points for cardiac transition energy and cardiac work for normals (N) and patient (P)
Figure 3E:
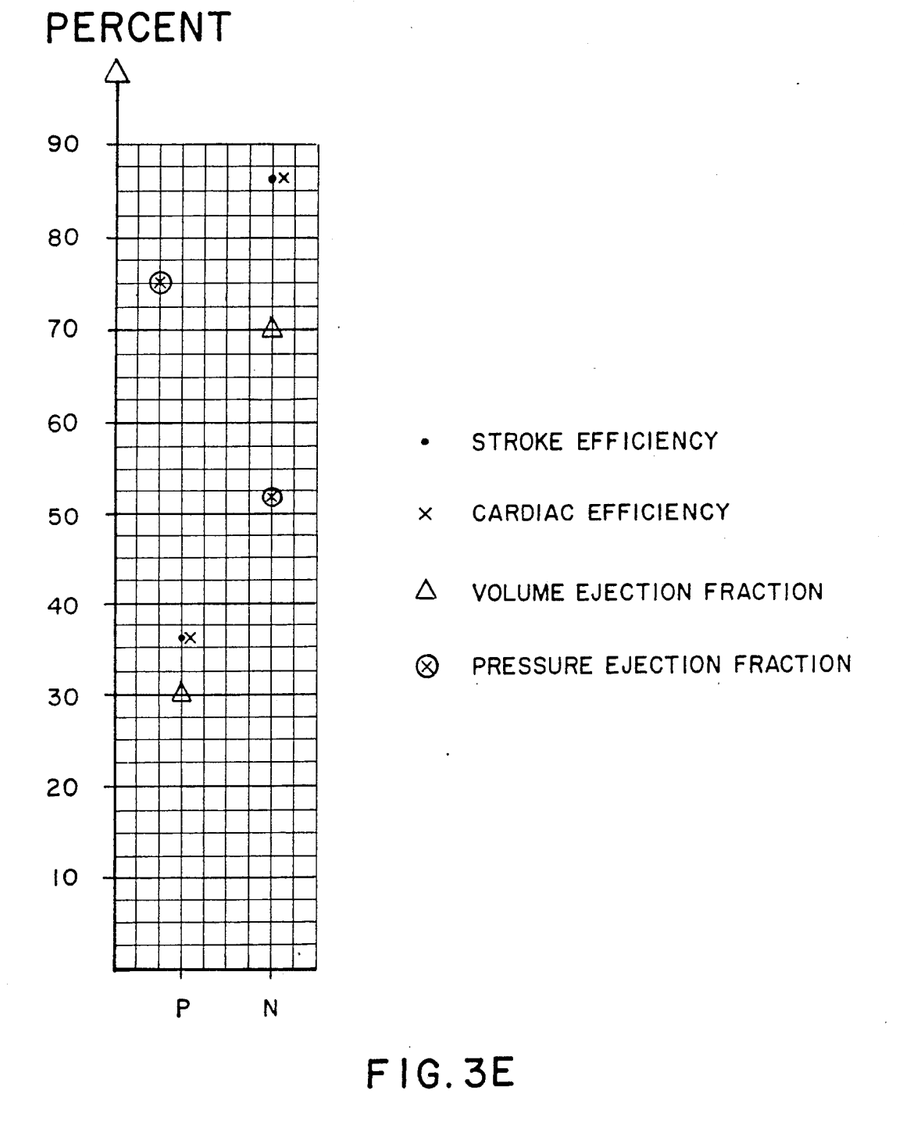
FIG. 3E illustrates plot points for the volume and pressure ejection fractions, and stroke and cardiac efficiencies for normals (N) and patients (P)

Referring to FIG. 3E the stroke efficiency (SEF) equals the ratio of the stroke transition energy over the highest preload potential which was necessary to accomplish this transition. Accordingly, SEF=[(EDVI * SBP)−(ESVI * DBP)−OL] / (EDVI * SBP) which equals STE/(EDVI * SBF). The quantity, SEF equals 86% for the normal (N) and 36% for the patient (P). Customarily, the events occurring with each heart beat are converted into events occurring each minute by multiplication of the per beat events by the heart rate HR. The cardiac preload band is defined by the preload potentials (EDVI * SBP * HR) and (EDVI * DBP * HR.), the preload / afterload band separation OL=−(EDVI * DBP * HR)−(ESVI * SBP * HR). Cardiac preload-and afterload potentials are graphically shown in FIG. 3C. Again it can be seen cardiac preload and afterload bands are separated for the Normal (N) by a value of 0.04 k. cal/h sq m. In contrast for the patient (P), there is an overlap between the cardiac preload-and afterload. The overlap is a value of 0.49 k cal/h sq. m where h=hours.

The cardiac transition energy CTE=(EDVI * SBP * HR)−(ESVI * DBP * HR)−OL, cardiac efficiency (FIG. 3E) CEF=CET/ (EDVI * SBP * HR), and cardiac deficiency CDF−OL/ (EDVI * SBP * HR). Appropriate cardiac values for a normals (N) and a patient (P) are listed in table 3 and are shown in FIG. 3D.

Total body oxygen consumption VO$_2$ or metabolic rate is determined by the activity a subject performs. The more strenuous the activity, the more oxygen will be consumed. Conversely, the minimum oxygen consumption required to sustain life at rest is defined as basal metabolic rate (BMR) which is a constant determined by age, sex and ambient temperature. For example, BMR=38 kcal/h sq m for a male subject at room temperature. VO$_2$ of an anesthetized patient equals BMR. Since BMR represents the total body oxygen consumption which is representative of the entire circulatory system, the cardiac preload-, afterload potentials, and the cardiac transition energy may be compared to the total circulatory requirements as measured by the BMR to yield circulatory data as follows: (EDVI * SBP * HR) / BMR and (EDVI * DBP * HR) / BMR define the circulatory preload band, (ESVI * SBP * HR) / BMR and (ESVI * DBP * HR) / BMR define the circulatory afterload band. The circulatory efficiency CIEF, equals the ratio of cardiac transition energy to BMR. CIEF=CTE / BMR. The circulatory deficiency equals the ratio of the cardiac preload/afterload band overlap to the BMR of CIDF=OL / BMR.

Figure 3F:
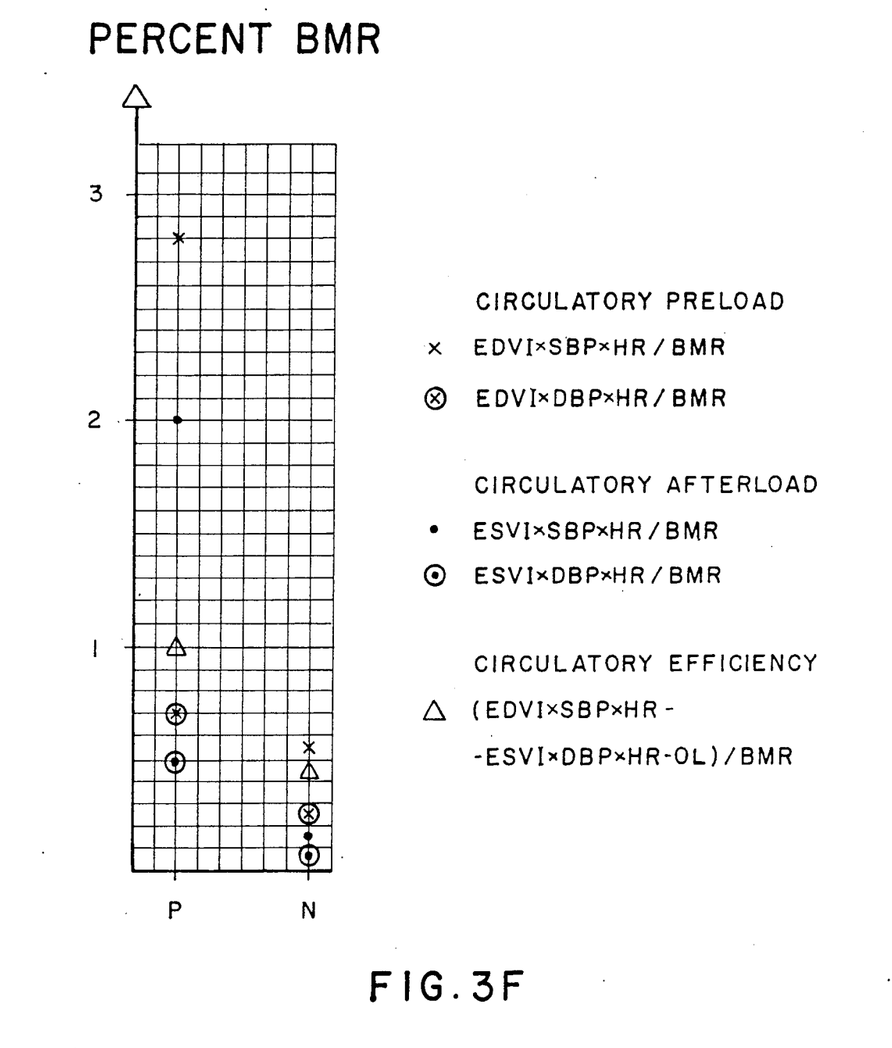
FIG. 3F illustrates plot points for the circulatory preload and circulatory afterload potentials, and circulatory efficiency for normals (N) and patients (P)

Readily apparent from FIGS. 3A, 3C and 3F is the separation of the preload band from the afterload band in a normals (N) and the overlap of preload band and afterload band in patients (P) with the consequent decrease of efficiency as the result of the band overlap as shown in FIGS. 3E and 3F. The preferred embodiment of the instant invention is used to tailor medical interventions in a patient-specific manner so as to affect preload and/or afterload and to reduce o eliminate the band overlap.

Figure 4:
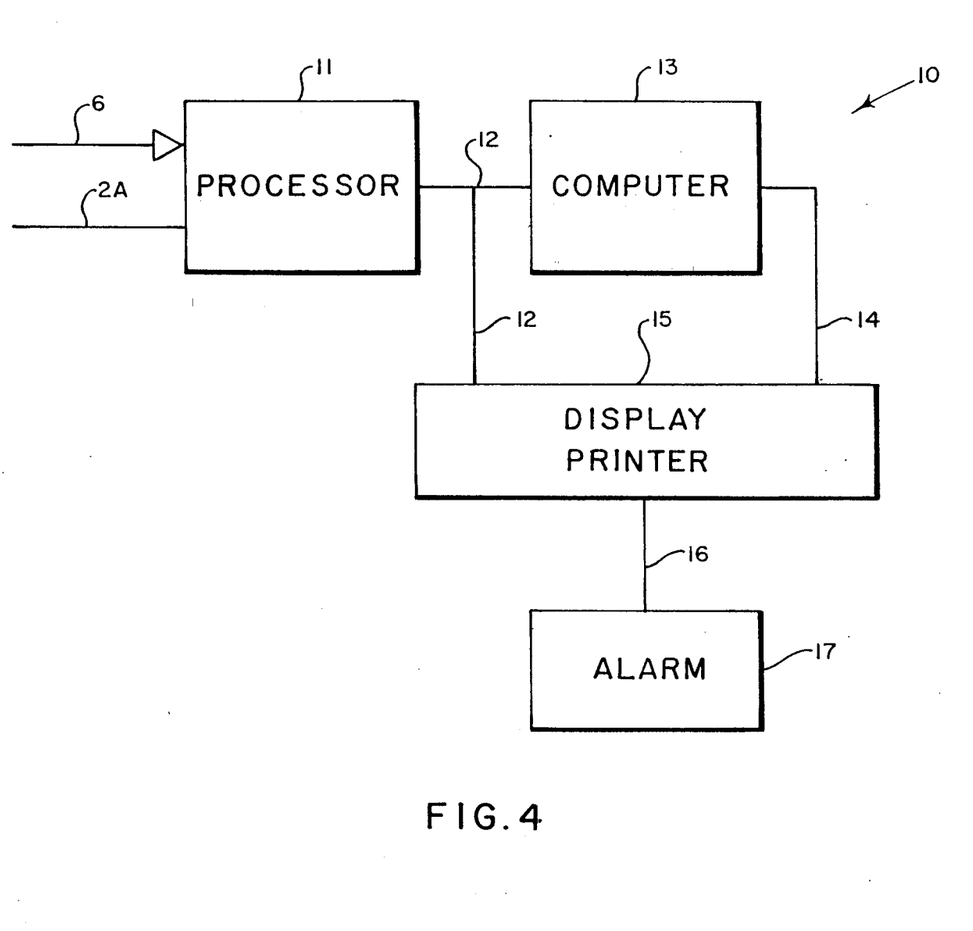
FIG. 4 is a block diagram of an electrical circuit for processing electrical signals according to the one embodiment of the present invention.

Illustrated by the block diagram of FIG. 4 is the cardiac efficiency monitoring apparatus 10 of the present invention. Signals representative of SBP, DBP, HR, temperature changes due to thermodilution injections, are carried by in multi-wire cable 2A and signals corresponding to oxygen content of inspired and expired air are carried by multi-wire cable 6 as inputs to a signal processor 11. Processor 11 delivers on a multi-wire line 12 signals produced as described hereinbefore corresponding to SBP, DBP, EDV, ESV, HR, and V0$_2$ as derived from the temperature changes sensed by the thermistor 3 in the catheter 2 and by a mask 4 placed on the subject's nose and mouth. The signals in multi wire line 12 are supplied to a computer 13 and to a display/printer 15. By simple program, the computer 13 calculates stroke index, volume ejection fraction, pressure ejection fraction, stroke work, cardiac work, stroke preload-, stroke afterload potentials, stroke band separation, stroke transition energy, stroke efficiency, stroke deficiency, cardiac preload-, cardiac afterload potentials, cardiac band separation, cardiac transition energy, cardiac efficiency, cardiac deficiency, circulatory preload-, circulatory afterload potentials, circulatory efficiency, and circulatory deficiency and delivers signals corresponding to the each derived valve by a multi-wire line 14 to a display/printer 15 where the calculated values represented by each electrical signal may be displayed or printed in numerical or graph form together with the signals supplied by multi-wire line 12. An alarm 17 is coupled to display 15 via line 16 to be activated when a predetermined value of a preselected one of derived signals described in this instant invention indicate a health hazard is attained.

Figure 5:
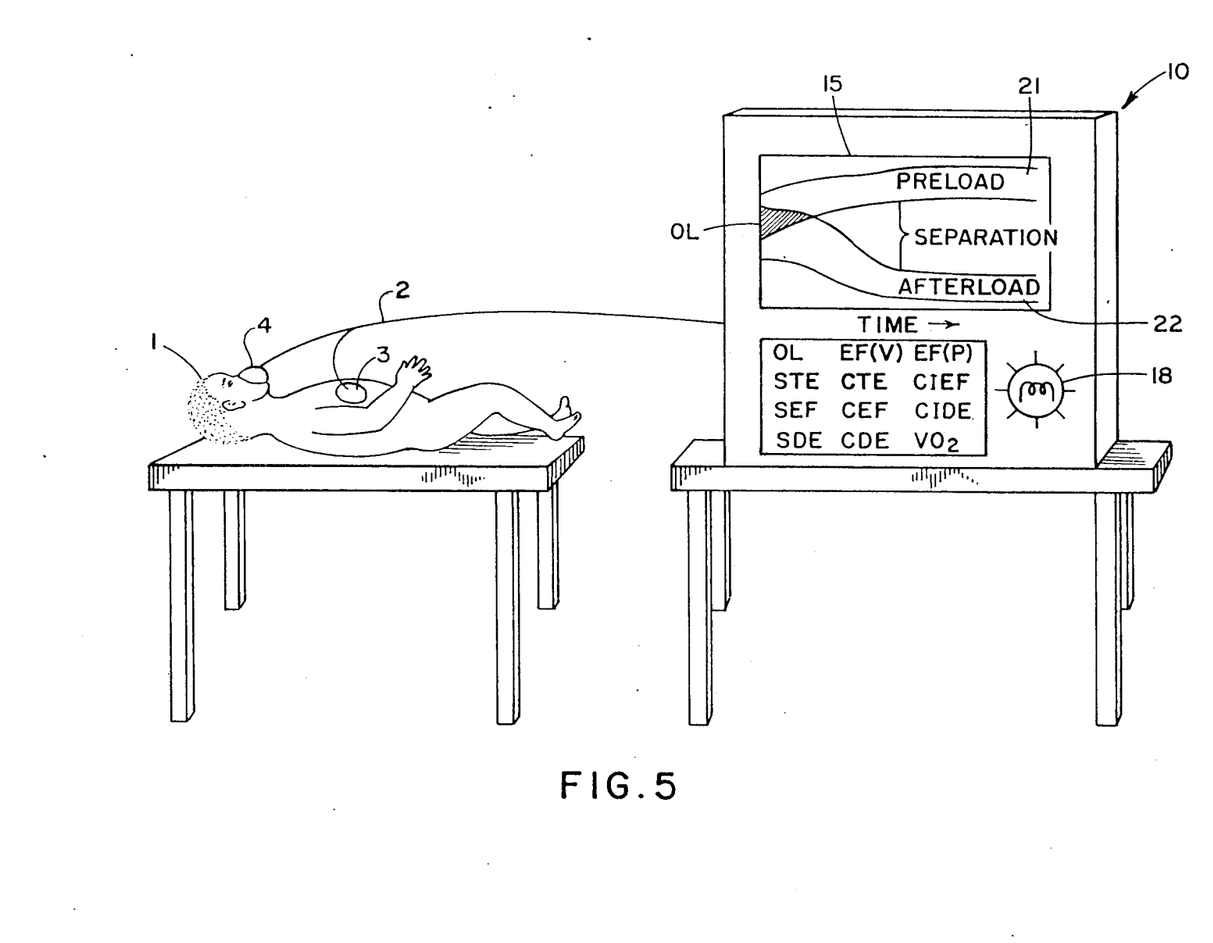
FIG. 5 is a schematic illustration of a monitoring system display according to the preferred embodiment.

In the embodiment of FIG. 5, a preferred form of display for the cardiac efficiency monitoring apparatus 10 is illustrated for monitoring progress or detecting regress of a patient on the basis of stroke efficiency, cardiac efficiency, separation or overlap of the preload and the afterload bands, stroke, cardiac, and circulatory efficiency, and stroke, cardiac, and circulatory deficiency. Since EDV and ESV signal are determined only intermittently by thermodilution injection of a cold bolus, but signals corresponding to SBP and DBP are measured continuously, attainment of predetermined pressure ejection fractions may trigger an alarm for performance of a thermodilution injection to update cardiac and circulatory efficiency. The overlap condition (OL) is all important and to be avoided. A normal separation of preload band display 21 and afterload band display 22 is an objective to be accomplished by medical intervention.

While the present invention has been described in connection with the preferred embodiment for the right heart using pulmonary artery catheters, it is to be understood that other similar embodiments such as the use of bioimpedance-, or echocardiographically-derived EDV and ESV signals, including left ventricular volume and pressure parameters (arterial blood pressures) as well as right ventricular parameters, or modifications and alterations may be made to perform the same functions of the present invention. Therefore, the present invention should be construed in breadth and scope in accordance with the claims as recited.

I claim:

1. A cardiac monitoring device for determining efficiency of the heart of an individual, said device including:

means for generating volume and pressure signals representative of end systolic volume, end diastolic volume, systolic blood pressure, and diastolic blood pressure, and means responsive to said signals for producing signals representing stroke preload and afterload potentials for determining efficiency of the heart.

2. The cardiac monitoring device according to claim 1 wherein said means for generating signals produce energy level signals representing the products of, (EDV * SBP), (EDV * DBP), (ESV * SBP), AND (ESV * DBP), where:

EDV is end diastolic volume;
   SBP is systolic blood pressure;
   DBP is Diastolic blood pressure; and
   ESV is end diastolic volume.

3. The cardiac monitoring device of claim 1 wherein the signals generated by said means to generate signals include signals representing the oxygen content of inspired and expired air and heart rate.

4. The Cardiac monitoring device according to claim 3 wherein said means for generating signals produce energy level signals representing the product of (EDV * SBP * HR), (EDV * DBP * HR), (ESV * SBP * HR), and (ESV * DBP * HR), where:

EDV is end diastolic volume;
   SBP is systolic blood pressure;
   DBP is diastolic blood pressure;
   ESV is end systolic volume; and
   HR is heart rate.

5. The cardiac monitoring device according to claim 3 whereas said means for generating signals produce signals representing oxygen consumption and basal metabolic rate.

6. The cardiac monitoring device of claim 3 wherein said means for generating signals operates to produce signals representing stroke efficiency defined as the ratio of stroke transition energy divided by the maximum stroke preload value, cardiac efficiency defined as the ratio of the cardiac transition energy divided by the maximum cardiac preload value, circulatory efficiency defined as the ratio of the cardiac transition energy divided by the metabolic rate, circulatory preload bands defined as the ratio of cardiac preload divided by the metabolic rate, circulatory afterload defined as the ratio of cardiac afterload divided by metabolic rate, stroke deficiency defined as the ratio of the stroke preload-afterload band overlap divided by maximum stroke preload potential, cardiac deficiency defined as the ratio of cardiac preload-afterload band overlap divided by maximum cardiac preload potential, and circulatory deficiency defined as the ratio of cardiac preload-afterload band overlap divided by metabolic rate, pressure ejection fraction defined as the difference of systolic blood pressure minus diastolic blood pressure all divided by the systolic blood pressure and volume ejection fraction defined as the difference of end distolic volume minus end systolic volume divided by end distolic volume.

means responsive to the signals generated by said means for producing signals for display of stroke and cardiac pre-and afterload bands, band separation and/or overlap, stroke and cardiac transition energies, stroke-, cardiac-, and circulatory efficiencies, circulatory pre-and afterload bands, stroke-, cardiac-, and circulatory deficiencies, pressure and volume ejection fraction data in numerical and graphical trend form; and means for causing an alarm at the attainment of a value of a predetermined one of the signals produced by said means for producing.

7. The cardiac monitoring device of claim 1 further including means to delineate the stroke and cardiac preload and afterload potential bands from the energy levels, said means to display displaying the separation or overlap of preload and afterload bands and the transition energies released in transitions between the preload and afterload band.

8. The Cardiac monitoring device of claim 7 wherein said means for generating signals operates to produce signals representing stroke and cardiac transition energies.

9. A method of diagnosing cardiac efficiency of an individual and monitoring progress or regress, including the steps of:
generating volume and pressure signals representative of end diastolic volume, end systolic volume, systolic blood pressure and diastolic blood pressure,
using said signals to establish energy levels in a cardiac cycle representing stroke and cardiac preload and afterload potential bands; and
using signals representing said stroke and cardiac preload and afterload potential bands to establish values representative of separation and/or overlap of stroke and cardiac preload and afterload bands.

10. The method according to claim 9 wherein said step of using said signals includes establishing values for stroke transition energies released in transition between the preload and after load bands.

11. The method according to claim 9 including the step of generating a heart rate signals corresponding to heart rate and using said heart rate signal and said volume and pressure signals to generate cardiac transition energies released in transitions between preload and afterload bands.

12. The method according to claim 11 including using said volume and pressure signals and a signal representing said overlap to generate a signal representative of stroke efficiency.

13. The method according to claim 11 including using said volume and pressure signals, said heart rate signal and a signal representing said overlap to generate a signal representing cardiac efficiency.

14. The method according to claim 11 including the further step of generating a metabolic rate signal and using said metabolic rate signal, said volume and pressure signals, said heart rate signal and a signal representing said overlap to generate a signal representing circulatory efficiency.

15. The method according to claim 11 including the further step of generating a metabolic rate signal and using said metabolic rate signal and signals representing said stroke preload and afterload potential bands to generate a signal representing circulatory preload and after load bands.

16. The method according to claim 11 including the step of generating a signal representing cardiac deficiency by using a signal representing said overlap and said pressure, volume and heart rate.

17. The method according to claim 9 including the step of generating a metabolic rate signal.

18. The method according to claim 17 wherein said step of generating a metabolic rate signal includes generating signals corresponding to the oxygen content of inspired and expired air.

19. The method according to claim 9 including generating a signal representative of stroke deficiency by using a signal representing said overlap and said volume and pressure signals.

20. The method according to claim 9 including the further step of using said volume signals to produce a signal representing a volume ejection fraction.

21. The method according to claim 9 including the further step of using said pressure signal to produce a signal representing a pressure ejection fraction.

* * * * *